United States Patent
Rietzel

(10) Patent No.: US 8,039,822 B2
(45) Date of Patent: Oct. 18, 2011

(54) PARTICLE THERAPY APPARATUS AND METHOD FOR MODULATING A PARTICLE BEAM GENERATED IN AN ACCELERATOR

(75) Inventor: Eike Rietzel, Darmstadt (DE)

(73) Assignee: Siemens Aktiengesellschaft, Munich (DE)

( * ) Notice: Subject to any disclaimer, the term of this patent is extended or adjusted under 35 U.S.C. 154(b) by 275 days.

(21) Appl. No.: 12/381,497

(22) Filed: Mar. 12, 2009

(65) Prior Publication Data

US 2009/0230327 A1    Sep. 17, 2009

(30) Foreign Application Priority Data

Mar. 14, 2008   (DE) .......................... 10 2008 014 406

(51) Int. Cl.
A61N 5/00 (2006.01)

(52) U.S. Cl. ................ 250/492.3; 250/492.1; 250/492.2

(58) Field of Classification Search ............... 250/492.1, 250/492.2, 492.3, 493.1
See application file for complete search history.

(56) References Cited

U.S. PATENT DOCUMENTS

| | | | |
|---|---|---|---|
| 2005/0167616 A1 | 8/2005 | Yanagisawa et al. |
| 2006/0017015 A1 | 1/2006 | Sliski et al. |

FOREIGN PATENT DOCUMENTS

| | | |
|---|---|---|
| DE | 19907098 A1 | 8/2000 |
| DE | 10031074 A1 | 1/2002 |
| WO | WO 2008/003527 A1 | 1/2008 |

*Primary Examiner* — David A Vanore
*Assistant Examiner* — Hanway Chang

(57) ABSTRACT

The invention relates to a particle therapy apparatus having an accelerator for generating a particle beam, a passive energy modulator comprising an absorber element, and a control entity. The control entity is designed to switch between an active adjustment of the energy in the accelerator and a passive energy modulation by the energy modulator, for the purpose of changing the energy of the particle beam from a high energy level to a low energy level in a step-by-step manner. In particular, this has the effect of shortening the dead times when changing between the energy levels.

18 Claims, 1 Drawing Sheet

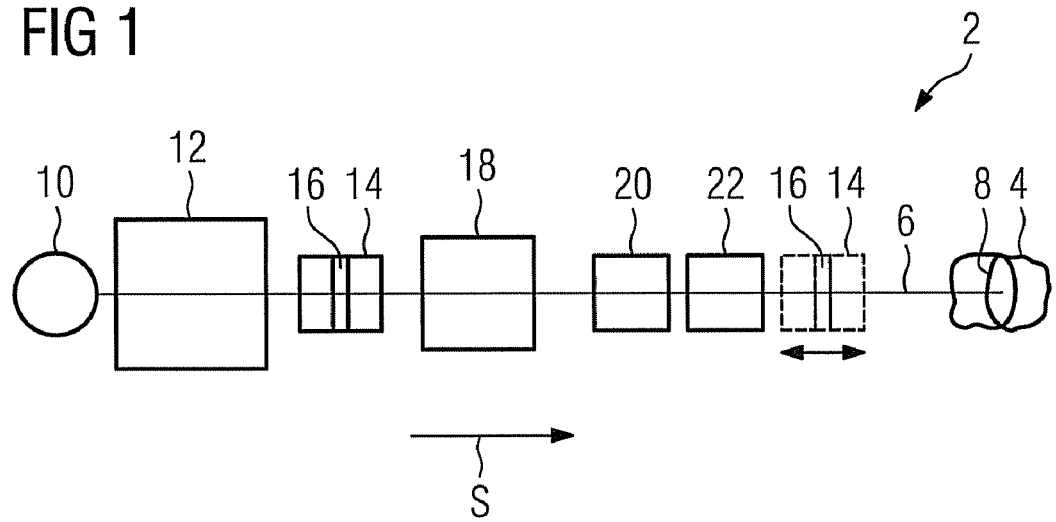
FIG 1
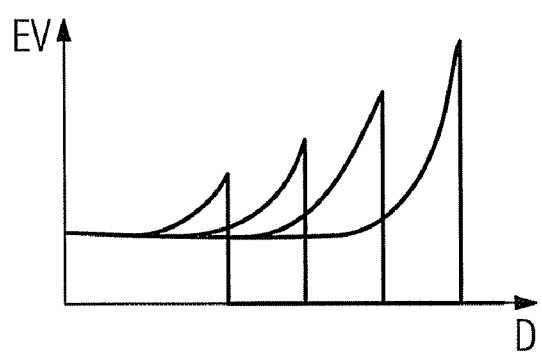
FIG 2
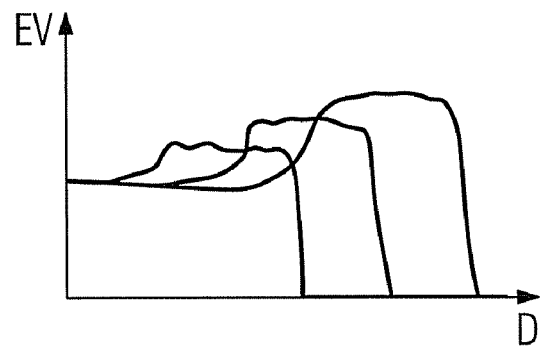

PARTICLE THERAPY APPARATUS AND METHOD FOR MODULATING A PARTICLE BEAM GENERATED IN AN ACCELERATOR

CROSS REFERENCE TO RELATED APPLICATIONS

This application claims priority of German application No. 10 2008 014 406.1 filed Mar. 14, 2008, which is incorporated by reference herein in its entirety.

FIELD OF THE INVENTION

The invention relates to a particle therapy apparatus comprising an accelerator for generating a particle beam. The invention further relates to a method for modulating a particle beam which is generated in an accelerator.

BACKGROUND OF THE INVENTION

In the context of particle therapy, of cancers in particular, a particle beam of e.g. protons or heavy ions, e.g. carbon ions, is generated in a suitable accelerator. The particle beam is guided in a beam guide in a treatment room, where it occurs via an emergence window. In a particular embodiment, the particle beam can be directed from an accelerator into different treatment rooms-alternately. In the irradiation room, a patient who is to undergo therapy will be positioned on a patient table and immobilized if applicable.

In order to achieve particularly good capacity utilization of the particle therapy apparatus, in particular of the accelerator, the particle beam is guided into different irradiation rooms consecutively in order to utilize the time before and after the irradiation of a patient, e.g. the time which is required for positioning the patient in an irradiation room, by irradiating another patient in another irradiation room.

The irradiation of the target region, usually a tumor, is normally done in layers. Depending on its energy, the particle beam reaches different depths in the tissue, such that the tissue can effectively be divided into slice-like sections or layers of identical penetration depth. The focused particle beam is then moved over the individual layers of the target region, this being known as "beam scanning", such that a plurality of points within a layer are irradiated, said points being located on a raster grid, for example. By means of correctly selecting the beam intensity or the energies, it is also possible accurately to irradiate regions having a complex shape. The arrangement of the layers and points to be irradiated is selected such that the planned dose distribution can be achieved.

The measures that are described can be utilized in the context of various scanning methods.

In the context of the so-called spot scanning method, the particle beam is directed at each target point for a predetermined time and/or deposits a predetermined number of particles at each target point, and is switched off while deflection magnets etc. are adjusted to a next target point.

In the context of the so-called raster scanning method, the particle beam is directed at each target point for a predetermined time period or deposits a predetermined number of particles at each target point, but is not or not always switched off between the target points.

In the context of so-called continuous scanning methods, the target points form contiguous lines, i.e. continuous (or quasi-continuous) sets, their number being countably infinite. In the context of a continuous scanning method, the particle beam is continuously deflected at least within a line or row in an isoenergy layer, and scans the target points without lingering at individual locations. Using a depth modulation device, it is also possible to carry out a continuous scanning method in which the penetration depth of the particle beam is continuously modulated.

The movement of the beam and the adjustment of the beam energy are controlled by a control entity. The range of the particle beam is normally varied using an energy adjustment at the accelerator by means of the control entity, this being known as active energy variation. In this case, the active energy variation requires the magnetic strength to be adjusted to the energy of the beam, generally at all magnets or at least at many magnets in the subsequent high-energy beam transport path. In this case, alteration times occur in which no beam can be applied, even though the time is required for the purpose of irradiation. The energy alteration time between two successive energy levels or layers in the target region, i.e. the dead time during the energy alteration, is usually approximately 1-2 s. In the case of a plurality of energy alteration operations, the total dead time then amounts to several seconds or even to more than a minute.

SUMMARY OF THE INVENTION

The invention addresses the problem of allowing an optimization of the irradiation times of a particle therapy apparatus.

The problem is solved according to the invention by means of a particle therapy apparatus having an accelerator for generating a particle beam and a so-called passive energy modulator comprising an absorber element, and having a control entity which is designed to switch between an active adjustment of the energy in the accelerator and a passive energy modulation, using energy absorption in particular, by means of the energy modulator, for the purpose of changing the energy of the particle beam from a high energy level to a low energy level (or vice versa) in a step-by-step manner.

The invention takes as its starting point the idea that an improvement in the irradiation time required for treating a patient is achieved by virtue of the dead time for the alteration from one energy level to the next being shortened because the passive energy adjustment can be carried out much more quickly than the active energy adjustment. Between the high energy level and the low energy level are a plurality of energy stages which are successively set in a plurality of steps, wherein an energy alteration operation is required between any two consecutive energy stages. The energy stages correspond to different isoenergy layers, for example. In order to reduce the dead times in this case, the energy alteration is not done exclusively actively via the accelerator, but instead some of the energy alteration operations are carried out by means of passive absorption with the aid of the energy modulator. The accelerator continues to be used for energy variation in this case, but fine stepping of the energy level—e.g. for the fine stepping of the energy level for individual isoenergy layers—is carried out by the supplementary energy modulator. The particle beam can be briefly interrupted during the switching times for the energy modulator. However, it is also possible for the irradiation to remain uninterrupted, particularly in the case of very quick switching times. An accelerator unit which allows an active adjustment of the energy can take the form of an accelerator that is composed of a plurality of components, for example. This can be a synchrotron with a preconnected linear accelerator, for example. The accelerator unit follows the high-energy beam transport path. The active energy variation by means of the accelerator requires magnets in the subsequent high-energy beam transport path to be adjusted to the new energy of the particle beam, wherein said adjustment also contributes significantly to the described dead times.

The energy modulator comprises an absorber element which is designed in particular in the form of a plate, or one or more wedges, and is arranged in the beam path. The material of the plate, e.g. Plexiglas or graphite, absorbs part of the energy of the particle beam and therefore changes the effective range of the beam in the patient. In this case, the range change depends on the thickness of the absorber element in the beam direction.

By virtue of the proposed addition to an active energy adjustment in the accelerator by a passive energy modulation using one or more energy modulators, the advantages of both approaches are combined. On the one hand, the effects of secondary radiation are kept at a low level due to the active energy adjustment. On the other hand, the time for energy alteration between the layers is reduced because an adjustment of a new energy level using the energy modulator clearly shortens the dead times. When the accelerator is used to full capacity, the shortened treatment duration therefore results in a higher patient throughput in particular.

According to a preferred embodiment, the control entity is configured to switch between the active adjustment of the energy of the particle beam and the passive energy modulation iteratively in an alternating sequence. This results in a monitored application of both energy alteration approaches, the number of operations for active adjustment and the number of subsequent passive energy modulations being predetermined. At the start of the irradiation, e.g. the high energy level is set by means of the accelerator. After "beam scanning" the corresponding layer of the tissue to be treated, the energy of the particle beam is reduced by one stage in order to irradiate a further layer. In this case, the reduction of the energy can be done either actively or passively. With regard to shortening the dead times to the greatest possible extent, and in consideration of the secondary radiation that occurs in the case of passive energy modulation, an optimal number of active and passive operations for energy modulation is calculated in order to determine which operations are applied in a defined, alternating sequence.

The control device is preferably configured so as to effect a passive energy modulation by means of the energy modulator at each second step. In this context, each active energy modulation in the accelerator is followed by a single step for passive energy modulation. As a result of the high number of steps for active energy adjustment, very little secondary radiation occurs, and therefore this operating mode of the particle therapy apparatus causes very little detrimental effect to the environment or even the patient.

With regard to a significant reduction in the dead times when switching between two adjacent energy stages of the particle beam, the control entity is alternatively configured so as to effect a change of the energy by means of the energy modulator more frequently than with the aid of the active adjustment in the accelerator, in particular in a ratio of 2:1. This means that each step of the active energy modulation is followed by two or more steps of the passive energy modulation, before the energy of the particle beam is varied by means of the accelerator again. In the case of two-stage or multi-stage passive modulation of the energy of the particle beam, use is made in particular of a plurality of absorber elements of different thicknesses, which are exchanged automatically. In order to weaken the energy of the particle beam further, combinations of two or more absorber elements are also possible.

A plurality of energy modulators are advantageously arranged at different positions of the beam path, in particular such that at least one beam guide element is arranged between the different energy modulators. An adjustment of the energy of the particle beam is then effected by the passive modulation of one or more passive energy modulators in addition to the active energy adjustment. One energy modulator can be arranged e.g. directly after the accelerator and a second as closely as possible to the patient, in particular behind a beam emergence window in the beam direction. For example, a passive energy modulator can also be positioned in front of redirection magnets next to a patient-based arrangement. This has the advantage that the particle beam is cleaned of scattered radiation caused by the redirection magnets.

It is also advantageous to provide a plurality of absorber elements of different absorption capacities, in particular different thicknesses, for the energy modulator, individually or in combination. In this context, it is possible to achieve a plurality of stages in the passive energy modulation. It is possible to utilize e.g. plates having a thickness of 1 mm and 2 mm, wherein an absorption element having a thickness of 3 mm is formed by a combination of these plates. A different absorption capacity can also be achieved by utilizing various materials.

The energy modulator is advantageously mounted such that it is mobile. For example, the energy modulator is arranged between the beam emergence window and the patient, and is moved as near to the patient as possible in order to restrict scatter effects.

Provision is preferably made for means whereby the geometric expansion of the particle beam can be changed. In order further to accelerate the treatment of a patient, a modification of the spatial energy distribution of the particle beam is additionally carried out in this context during the energy modulation in order to shorten the dead times, thereby resulting in a reduction in the layers that must be irradiated.

According to a preferred embodiment, the means comprise at least one ripple filter for expanding the energy distribution of the particle beam in the beam direction. A ripple filter features fine structures of an absorber material, whereby the particle beam is variously modulated in its energy. The scattering in the ripple filter causes the part regions of the beam having different energy to be mixed again on the path to the target region, thereby resulting in a quasi homogenous expansion of the energy distribution. When a ripple filter is used, the particle beam is therefore modified such that the curve which shows the energy loss over the penetration depth does not exhibit such a distinctive peak. Instead, the particles already lose a large part of their energy at a lesser penetration depth, this being graphically illustrated by a widened peak. This corresponds to an expansion of the layer that is effectively irradiated. Consequently, fewer beam operations are required in the beam direction, i.e. the number of layers to be irradiated in the tissue can be reduced by virtue of the expansion of the beam in the beam direction.

At the boundary of the tumor, where the tissue is healthy, it is particularly important that the fewest possible particles penetrate into the healthy tissue. In the range of the high and the low energy levels, these being provided for irradiation of the outermost layers which are surrounded by healthy tissue, it is therefore advantageous to set a beam that is less longitudinally expanded than in the energy midrange. In this context, different ripple filters are preferably provided for the different energy levels. In the range of the high and the low energy levels, provision is made e.g. for no ripple filter or for ripple filters which slightly influence the energy distribution of the particle beam, i.e. a beam which is less longitudinally expanded is set in these peripheral regions, such that a distinctive Bragg peak is formed in the curve profile in the graphical visualization of the energy distribution in the beam. For the tumor-internal layers, no clear delimitation relative to the adjacent layers is required. When irradiating these layers, it is therefore possible to use ripple filters which clearly expand the beam, such that the number of irradiation operations in the beam direction is reduced as described above.

A particularly high degree of automation, resulting in an additional acceleration of the irradiation, is achieved because the ripple filters are automatically exchangeable for the different isoenergy layers in the beam direction.

According to a further preferred embodiment, the means comprise a focusing device for changing the geometric expansion of the particle beam radially relative to the beam direction, and the control device is configured to vary a raster grid distance for the particle beam. In this context, the raster grid specifies the number and arrangement of the raster points, within a layer of identical particle range, which are irradiated at specific points by means of the particle beam during the "beam scanning". During the irradiation of a raster point, the number of particles is ascertained by means of a monitoring system. When the desired number of particles is reached, the control entity controls the particle beam such that the next raster point is irradiated. By means of the focusing device, the particle beam is radially expanded or less sharply focused, thereby increasing the size of the area that is struck by the particles. At the same time, fewer raster points are required within the layer. As a result of this, the quantitative monitoring is simplified in particular, and a prompt response of the control unit is allowed when the desired number of particles is reached, since more particles are now required per raster point due to the enlarged area and the monitoring system has sufficient time for counting, even if irradiation is faster than with a more sharply focused beam.

The control entity is advantageously configured to set a more sharply focused particle beam at the peripheral region of the raster grid than in the inner region of the raster grid. As a result of this, the adaptations of the beam focus are done dynamically, in order to achieve a marked peripheral drop in the particle dose at the periphery of the tissue layer and hence to conserve the adjacent healthy tissue as effectively as possible.

The problem is further solved according to the invention by means of a method having the features in claim 11. The cited advantages and preferred embodiments relating to the particle therapy apparatus apply analogously to the method.

For example, the active adjustment of the energy and the passive energy modulation can therefore be applied iteratively in an alternating sequence. In particular, the passive energy modulation can be used at every second step or the passive absorption can be used more frequently than the active adjustment.

BRIEF DESCRIPTION OF THE DRAWINGS

An exemplary embodiment of the invention is explained in greater detail below with reference to a drawing, in which:

FIG. 1 shows a greatly simplified schematic illustration of a particle therapy apparatus, and FIG. 2 shows the energy distribution of a plurality of particle beams in two diagrams, without and with a ripple filter for expansion of the particle beams in the beam direction.

DETAILED DESCRIPTION OF THE INVENTION

FIG. 1 shows a schematic diagram of a particle therapy apparatus 2. The particle therapy apparatus 2 is used to irradiate a tumor tissue 4 in a step-by-step manner with the aid of a particle beam 6, wherein a slice-shaped section 8, also referred to below as a layer, of the tumor 4 is treated at each step. The particle beam 6 is generated in an accelerator 10, which is controlled by a control unit 12. The accelerator 10 delivers the particles with an energy which is required for the layer 8 that must currently be irradiated. Inter alia, the control unit 12 comprises a raster scanning device (not shown here) which deflects the beam 6 in both horizontal and vertical directions in order to scan the tumor tissue 4 within the layer 8. The raster scanning device comprises e.g. two pairs of magnets for this purpose.

The beam 6 also passes through an energy modulator 14 which is arranged in the beam path. The energy modulator 14 comprises an absorber element 16 which absorbs part of the energy of the particle beam 6 when the particle beam 6 passes through its material, and therefore limits the range of the particles. The energy modulator 14 is therefore used for passive energy modulation by means of absorption. In this case, the energy modulator 14 can be arranged differently within the schematic structure shown for a particle therapy apparatus. It can also be located at any other position in comparison with the sequence of elements shown, e.g. directly in front of the patient, as illustrated in the figure by the broken-line block 14. For a possible arrangement of the passive energy modulation system 14 between beam emergence window and patient, it can preferably also be moved as near to the patient as possible, as indicated by an arrow, in order to limit scattering effects. A combination of two or more energy modulators 14 at different positions in the beam path is also possible.

The particle beam 6 then passes through a monitoring system 18 which is designed in the form of a particle counter in particular. The particle dose which is deposited in the region of the tumor 4 depends on the number of particles present in the beam 6. During the irradiation operation, the number of particles acting on the tumor 4 is ascertained by means of the monitoring system 18. When the desired number of particles in a raster point is reached, a signal is sent to the control entity 12, which positions the raster scanning entity such that the beam 6 is directed at the next raster point.

In the exemplary embodiment shown, means for changing the spatial energy distribution of the particle beam 6 are also provided further along the beam. According to the invention, these means comprise a ripple filter 20 for expansion of the beam 6 in the beam direction S and a focusing device 22 for expansion of the beam 6 radially relative to the beam direction S.

During the irradiation of the tumor 4 of a patient (not shown), the accelerator 10 sets a high energy level of the particle beam, such that the particle beam 8 reaches the right-hand peripheral region of the tumor 4 in the figure. In this case, a plurality of raster points of the layer 8 that is reached in the tumor 8 are irradiated at specific points. Instead of a tumor, the particle beam can also be directed at non-living materials, cell cultures or phantom material, as is frequently carried out in the context of research work or verification of beam parameters, for example.

In order to set a new, lower energy level for irradiating a further layer, which in this case is situated to the left of the right-hand peripheral region in the interior of the tumor 4, the energy of the particle beam 6 is reduced. This can be done in two ways—either by means of an active energy modulation in the accelerator 10 or passively using the energy modulator 16.

In order to reduce the dead times which occur in the case of a purely active energy alteration, in the case of the particle therapy apparatus 2 shown in FIG. 1, the active energy modulation is supplemented by passive energy absorption using the energy modulator 14, which requires less time to set a lower energy level. For example, an active energy alteration operation can be followed in each case by a passive energy alteration operation. When adjusting the energy of the beam 6, it is also possible alternately to perform coarse stepping by means of the accelerator 10, wherein subsequent fine stepping takes place in two or more energy stages via the energy modulator 14. In the present exemplary embodiment, the control entity 12 is configured to use the energy modulator 14 for the two subsequent energy alteration steps after each active energy adjustment in the accelerator 10. For this purpose, the energy modulator 14 comprises two absorber elements 16 of different thicknesses, which are exchanged automatically for the layer transition. After each further active energy adjustment, the absorber elements are used in the same sequence in order to reduce the energy of the particle beam 6 twice by stages.

In order further to accelerate the irradiation operation, thereby allowing in particular a higher patient throughput in the context of a greater efficiency of the particle therapy apparatus, use is also made of the ripple filter 20 and the focusing device 22. The effect of the ripple filter 16 is explained in greater detail in FIG. 2. In the diagrams according to FIG. 2, the energy loss EV is qualitatively plotted against the penetration depth D of the particle beam 6 in the tissue. In the upper diagram, the energy distribution for four layers 8 that are to be irradiated in the tumor 4 is shown when no ripple filter 20 is used. In this diagram, four Bragg peaks are therefore clearly recognizable.

In the lower diagram, the energy distribution of the beams 6 after a ripple filter 20 is shown. As a result of the filter 20, the peak of each energy distribution curve is expanded or spread, such that after the deeper layers have undergone a plurality of irradiation operations, sufficient particles have already reached the front layers in the tumor 4. For this reason, the tumor 4 can be divided into fewer layers 8 requiring irradiation, thereby accelerating the treatment.

When using ripple filters 20, the beam 6 can also be less expanded in the outermost layers in the peripheral region of the tumor, such that the effect of the irradiation is concentrated on the tumor 4 without excessively exposing the surrounding tissue. In this context, it is possible to use ripple filters 20 which slightly transform the Bragg peak in the curve of the energy profile, or the peripheral regions can be irradiated without a ripple filter 20. In particular, if there is a plurality of filters 20, these are exchanged automatically.

In order further to shorten the duration of the treatment, provision is made for a focusing device 22 in the exemplary embodiment shown. The width of the beam 6 is adjusted by means of the focusing device 22, i.e. it is focused more or less sharply. Moreover, the control entity 12 is designed in such a way that fewer raster points are irradiated within the layer 8 when the beam 6 is less sharply focused, i.e. wider. In the case of the focusing device 22, it is also the case that the raster points at the periphery of the layer 8 are irradiated using a more sharply focused beam 6, such that the surrounding healthy tissue is not included.

The invention claimed is:

1. A particle therapy apparatus, comprising:
an accelerator that generates a particle beam;
a passive energy modulator that performs a passive energy modulation of the particle beam; and
a control unit that switches between an active adjustment of energy in the accelerator and the passive energy modulation for changing energy of the particle beam between a high energy level and a low energy level step-by-step, wherein the control unit switches between the active adjustment of the energy and the passive energy modulation iteratively in an alternating sequence.

2. The particle therapy apparatus as claimed in claim 1, wherein the control unit controls the passive energy modulation at each second step.

3. The particle therapy apparatus as claimed in claim 1, wherein the control unit controls a change of the energy by the passive energy modulator more frequently than the active adjustment in the accelerator.

4. The particle therapy apparatus as claimed in claim 3, wherein the control unit controls the change of the energy by the passive energy modulator more frequently than the active adjustment in the accelerator in a ratio of 2:1.

5. The particle therapy apparatus as claimed in claim 1, wherein a plurality of passive energy modulators are arranged at different positions of a beam path.

6. The particle therapy apparatus as claimed in claim 5, wherein a beam guide element is arranged between the plurality of the passive energy modulators.

7. The particle therapy apparatus as claimed in claim 1, further comprising a device that changes a geometric expansion of the particle beam.

8. The particle therapy apparatus as claimed in claim 7, wherein the device comprises a ripple filter that expands the particle beam in a beam direction.

9. The particle therapy apparatus as claimed in claim 8, wherein the device comprises a plurality of different ripple filters for a plurality of different energy levels.

10. The particle therapy apparatus as claimed in claim 8, wherein the device comprises a focusing device that changes the geometric expansion of the particle beam radially relative to the beam direction and the control unit varies a raster grid distance for the particle beam.

11. The particle therapy apparatus as claimed in claim 10, wherein the control unit sets a more sharply focused particle beam at a peripheral region of the raster grid than in an inner region of the raster grid.

12. A method for modulating a particle beam, comprising:
generating the particle beam in an accelerator; and
changing energy of the particle beam between a high energy level and a low energy level step-by-step by an active adjustment of energy in the accelerator and a passive energy modulation in a beam path of the particle beam,
wherein the active adjustment of the energy and the passive energy modulation are applied iteratively in an alternating sequence.

13. The method as claimed in claim 12, wherein a geometric expansion of the particle beam is changed.

14. The method as claimed in claim 13, wherein the energy of the particle beam in the beam direction is expanded by a ripple filter.

15. The method as claimed in claim 14, wherein a beam that is less longitudinally expanded is set in a region of the high energy level and the low energy level than in a midrange energy level.

16. The method as claimed in claim 15, wherein a plurality of different ripple filters are provided for a plurality of different energy levels that are exchanged automatically.

17. The method as claimed in claim 13, wherein the geometric expansion of the particle beam is expanded radially relative to the beam direction and a raster grid distance for the particle beam is varied.

18. The method as claimed in claim 17, wherein a more sharply focused particle beam is set in a peripheral region of the raster grid than in an inner region of the raster grid.

* * * * *